United States Patent [19]

Guigan

[11] 4,314,968
[45] Feb. 9, 1982

[54] SIMULTANEOUS ANALYSIS APPARATUS

[76] Inventor: Jean Guigan, 9, rue Jean Mermoz, 75008 Paris, France

[21] Appl. No.: 198,323

[22] Filed: Oct. 20, 1980

[30] Foreign Application Priority Data

Oct. 26, 1979 [FR] France .................... 79 26615
Jan. 11, 1980 [FR] France .................... 80 00583
May 23, 1980 [FR] France .................... 80 11511

[51] Int. Cl.$^3$ .................. G01N 33/50; G01N 1/10; G01N 31/00; G01N 21/07
[52] U.S. Cl. ................... 422/64; 23/230 B; 422/72
[58] Field of Search .............. 422/64, 72; 233/26; 23/230 B

[56] References Cited

U.S. PATENT DOCUMENTS

| | | | |
|---|---|---|---|
| 3,681,029 | 8/1972 | Shapiro | 422/72 X |
| 3,873,217 | 3/1975 | Anderson et al. | 422/72 X |
| 4,148,607 | 4/1979 | Bernoco et al. | 422/72 X |
| 4,154,793 | 5/1979 | Guigan | 422/72 X |

*Primary Examiner*—Ronald Serwin
*Attorney, Agent, or Firm*—Sughrue, Mion, Zinn, Macpeak and Seas

[57] ABSTRACT

Analysis apparatus which uses a solid reaction support designed to hold successively a quantity of first reagent such as a biological liquid which contains the substance to be analysed, and then a quantity of second reagent which contains a protein on which is fixed a biological indicator. The apparatus is constituted by an analysis rotor (1) which includes firstly a plurality of peripheral cells (2) each of which contains said reaction support (3) and secondly means which allow a washing liquid to be conveyed towards each cell, each of said cells (2) being provided with a peripheral orifice (7) for removing liquid and having an upper portion provided with a reagent inlet orifice (8) and a lower portion which accommodates said reagent.

15 Claims, 10 Drawing Figures

SIMULTANEOUS ANALYSIS APPARATUS

The invention relates to an analysis apparatus of the type which uses a solid support designed to hold successively a quantity of first reagent such as a biological liquid e.g. serum or plasma which contains the substance to be analysed, then a quantity of second reagent which contains a protein on which a biological indicator is fixed, e.g. an enzyme or a radioisotope for radioimmunology.

BACKGROUND OF THE INVENTION

Present techniques use a solid support which is usually a spherical polystyrene bead covered with a protein (e.g. a polypeptide coming from a vaccinated animal) which has anti-body type properties. Said support is disposed in a test tube type receptacle into which a quantity of first reagent is admitted and, after an incubation period, the bead must be washed with water to remove the excess reagent. Said washing is manual as is the removal of the liquid, the tube being turned upside down and, the open end of the tube having tabs which prevent the bead from falling out. The operation must then be repeated with the second reagent, and its excess is again removed by washing, after which the tube is conveyed to an analysis unit proper, e.g. for photocolorimetric analysis by injecting a coloured reagent.

Although the principle of the support bead which successively holds the anticipated quantity of reagent is very simple and effective, the technique used gives little satisfaction. Indeed, the washing operations carried out by hand are not very reliable because washes and temperature conditions differ on different occasions, and they are unsuitable for analyses using grouped tests with different dosages because of the numerous handling operations which are necessary and introduce an inevitable risk for error.

The present invention aims to provide more reliable apparatus of simple design suitable for simultaneous analyses using several dosages and a minimum of handling.

SUMMARY OF THE INVENTION

This aim is achieved in accordance with the invention by analysis apparatus which uses a solid reaction support designed to hold successively a quantity of first reagent such as a biological liquid which contains the substance to be analysed, and then a quantity of second reagent which contains a protein on which a biological indicator is fixed. The apparatus is constituted by an analysis rotor which includes firstly a plurality of peripheral cells each of which contains said solid reaction support and secondly means which allow a washing liquid to be conveyed to each cell. Each of said cells is provided with a peripheral orifice for removing liquid and having an upper portion provided with a reagent inlet orifice and a lower portion which accommodates said reagent.

The analysis apparatus in accordance with the invention may also have at least one of the following features:

the means which convey the washing liquid are constituted by a central inlet orifice from which radial pipes leave and connect said central orifice to each of the peripheral cells; preferably, the radial pipes are in a plane which is essentially perpendicular to the axis of rotation of the apparatus and communicate with each cell substantially at the same level as the peripheral orifice through which liquid is removed from said cell;

the inlet orifices for the reagent are equidistant from the axis of the rotor;

the walls which define the lower portion of each cell allow simultaneous photometric analysis;

the rotor is formed by superposing two coaxial portions whose contacting peripheral edges define directly the peripheral orifices of the cells;

the reaction support is formed by at least one bead;

the bottom of each cell is generally inclined so that firstly the lower portion of the cell has a volume which is sufficient to accommodate the reaction support and the quantity of reagent which covers it and secondly said support is guided substantially up to the level of the peripheral orifice of said cell during centrifuging;

the support is constituted by a plurality of beads of very small dimensions, and a barrier is disposed in each cell adjacent said peripheral removal orifice, said barrier being suitable for retaining the beads during said centrifuging;

the inner and outer surfaces of the cells are substantially parallel, the outer surface further having a side spout ending in the removal orifice and allowing the complete removal of the washing liquid during centrifuging;

the reaction support is constituted by the wall of the lower portion of each cell.

DETAILED DESCRIPTION

Figure 1:
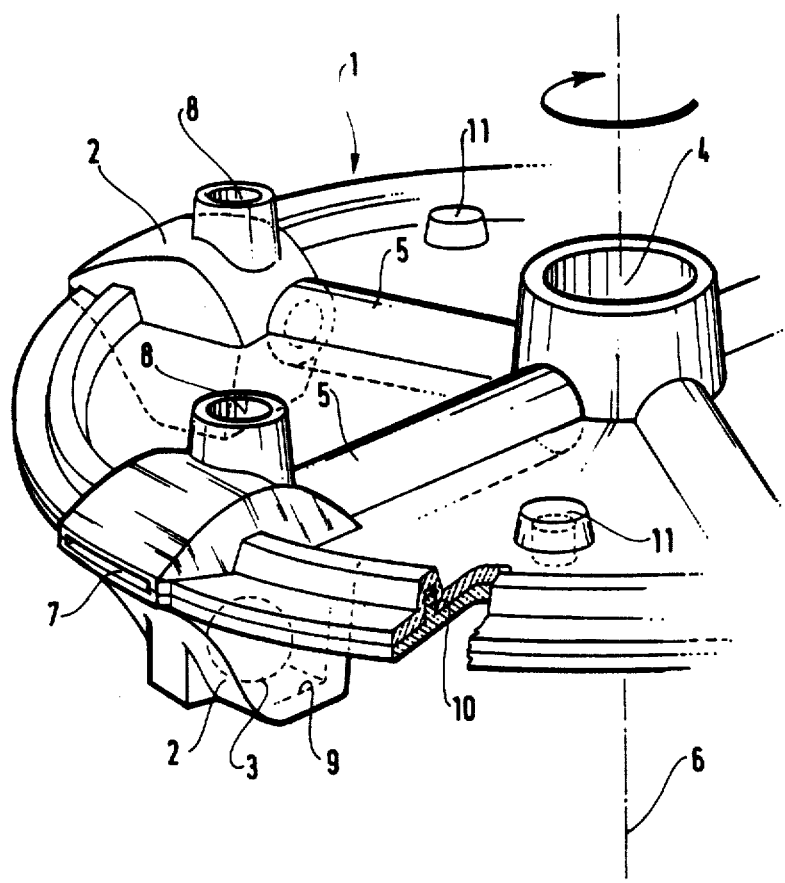
FIG. 1 is a partial perspective view illustrating analysis apparatus in accordance with the invention.
Figure 2:
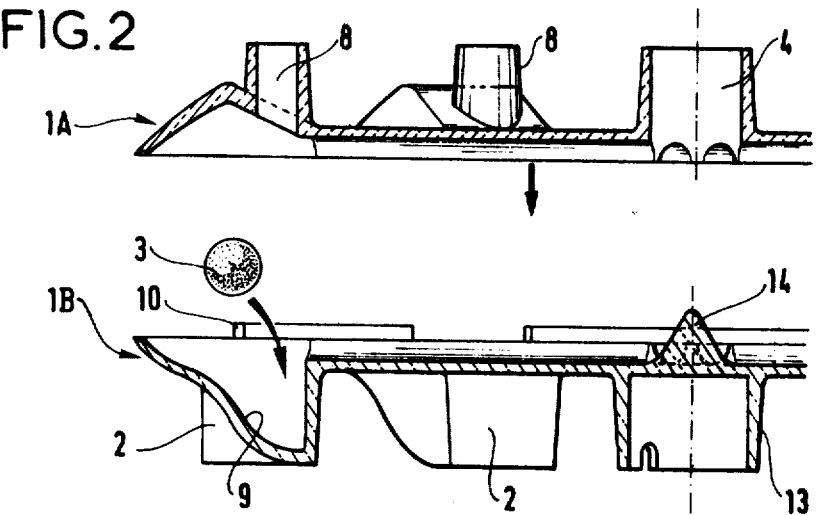
FIG. 2 is a partial exploded axial cross-section of the apparatus of FIG. 1.
Figure 3:
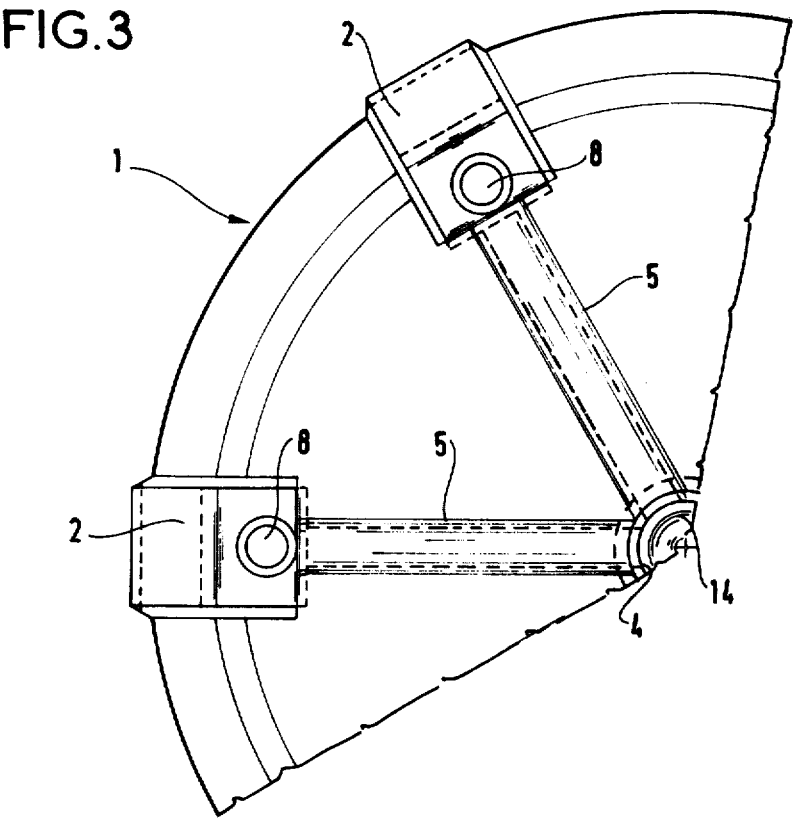
FIG. 3 is a partial top view of the same apparatus.

Apparatus in accordance with the invention is illustrated in FIGS. 1 to 3. It is constituted by a rotor 1 which includes firstly, a plurality of peripheral cells 2, each of which contains a conventional supporting bead 3 (made of polystyrene covered with a protein which has properties of the anti-body type) and secondly, means which allow a washing liquid to be conveyed towards each cell. There are several possibilities for conveying a washing liquid. The possibility illustrated here is particularly simple and effective, it comprises a central inlet orifice 4 which communicates with each peripheral cell 2 via respective radial pipes 5 which are in a plane essentially perpendicular to the axis of rotation 6 of the apparatus. An annular groove communicating with each peripheral cell via radial pipes could just as well be provided instead of the central orifice 4. It should be observed that the radial pipes 5 are here defined by two complementary portions formed on each of two parts 1A, 1B which together constitute the rotor 1 (see FIG. 2) but that any other type of pipe can be envisaged e.g. a flat edge on one portion of the rotor (hence its inner surface) and a groove on the other portion.

Further, each cell is provided with a peripheral orifice 7 for removal of liquids (here defined directly by superposition of the peripheral edges of both axial portions 1A, 1B which form the rotor 1) and has an upper portion provided with an inlet orifice 8 and with a bottom by which the bead 3 can be raised by centrifugal force substantially to the level of said peripheral orifice 7 when the apparatus rotates (this last characteristic will be explained further on with reference to FIGS. 4A, 4B, 4C).

The person skilled in the art can choose any suitable means for connecting and positioning the two portions 1A, 1B to constitute the rotor 1: the apparatus illustrated here by way of an example uses an annular groove 10 and centering studs 11, but numerous other possibilities can be envisaged.

The characteristics of the apparatus, in particular as far as concerns the shape of the cells, will be described at the same time as the operation of said apparatus so as better to understand the function they fulfill.

Figure 4A:
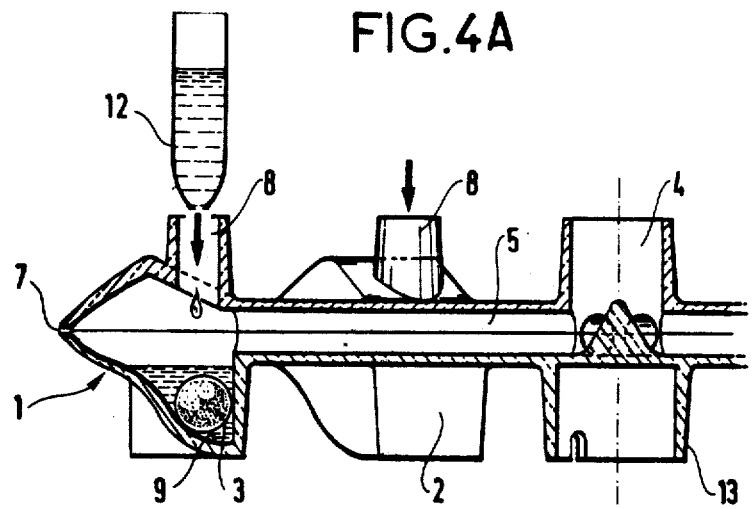
FIGS. 4A, 4B, 4C are sectional views which illustrate the operation of the apparatus of FIG. 1.

FIG. 4A illustrates the rotor which each of its peripheral cells 2 equipped with an associated bead 3 (each bead possibly corresponding to a particular dosage). The rotor is disposed beneath feed means-in this case a pipette 12-to inject a (preferably calibrated) volume of a first reagent into each cell. The first reagent may be a serum, a plasma or any other biological liquid which contains the substance to be analysed. After said injection, which can be obtained for example by making the rotor rotate successively through the corresponding angle to place each orifice 8 under the pipette 12, the liquid is allowed to stand during the required incubation period. It should be noted that the volume at the bottom 9 of each cell is sufficient to accommodate the bead and the reagent without the level of the reagent reaching the pipe 5.

Figure 4B:
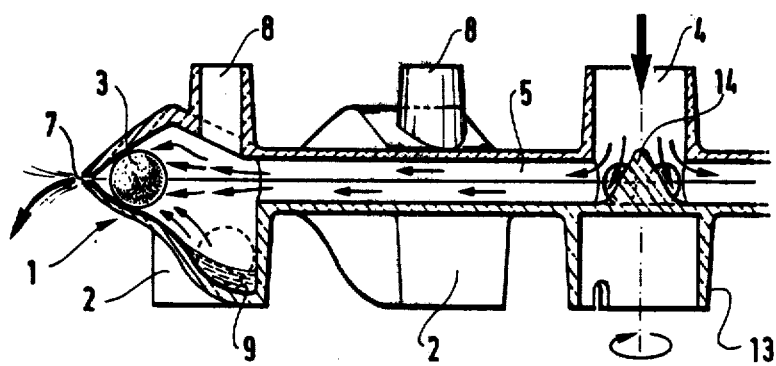

FIG. 4B illustrates the rotor during rotation. It is driven via a notched drive coupling 13 of an entirely conventional type. While the rotor rotates, washing liquid is injected via the central orifice 4. In each cell the effect of centrifuging is to drive out the excess reagent via the peripheral orifice 7 and to move the bead 3 up to the level of said peripheral orifice since the bottom 9 is generally inclined. Further, good distribution of the washing liquid is promoted by the presence of a central boss 14 in the central orifice 4. The washing liquid flows through the radial pipes 5 and thoroughly washes each bead 3 which is held in a favourable position for washing by the centrifugal force and the tapering shape of each cell. The washing liquid causes each bead to rotate during washing thereby washing it all over, and then escapes via the peripheral orifices 7.

Figure 4C:
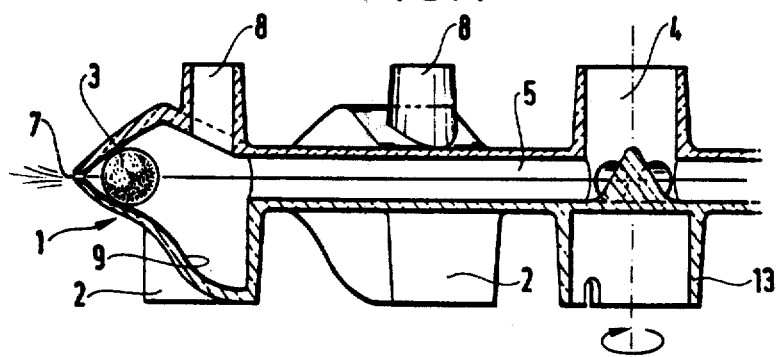

FIG. 4C illustrates an optional bead drying step consisting in closing the washing liquid inlet while continuing to centrifuge. It should be observed that such drying was practically impossible with previous apparatus without using complicated equipment, while here, it is very easy to perform.

The operations are then repeated with the second reagent which contains the protein having a biological indicator fixed to it, e.g. an enzyme or a radio-isotope. Then, as the rotor comes to rest, the beads drop to the bottoms of their respective cells and are ready for simultaneous analysis (the bottom walls of the cells being designed specifically for this purpose). The analysis may be direct using a Geiger counter if a radio-active indicator is used, or it may be indirect if a colored reagent is used, perhaps in conjunction with a reaction stopping agent.

Figure 5A:
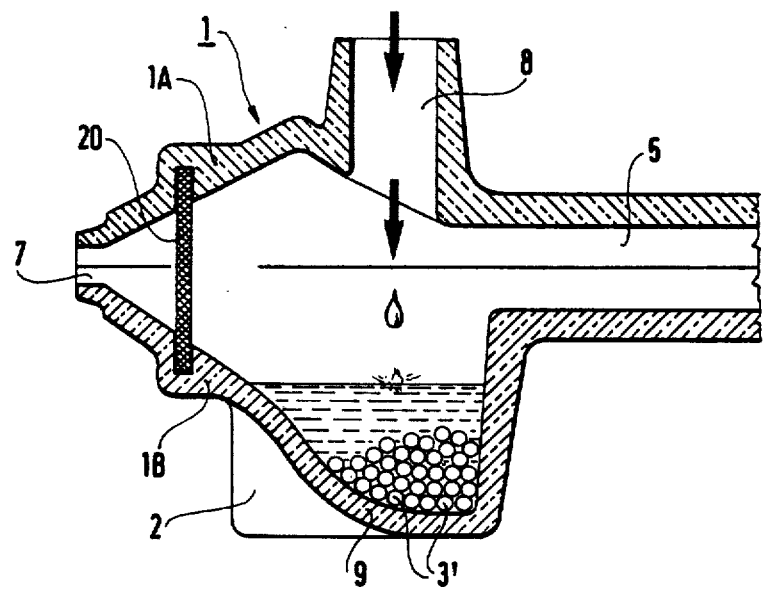
FIGS. 5A and 5B, are sectional views which illustrate the operation of the apparatus in the case where the cell contains a plurality of small beads.
Figure 5B:
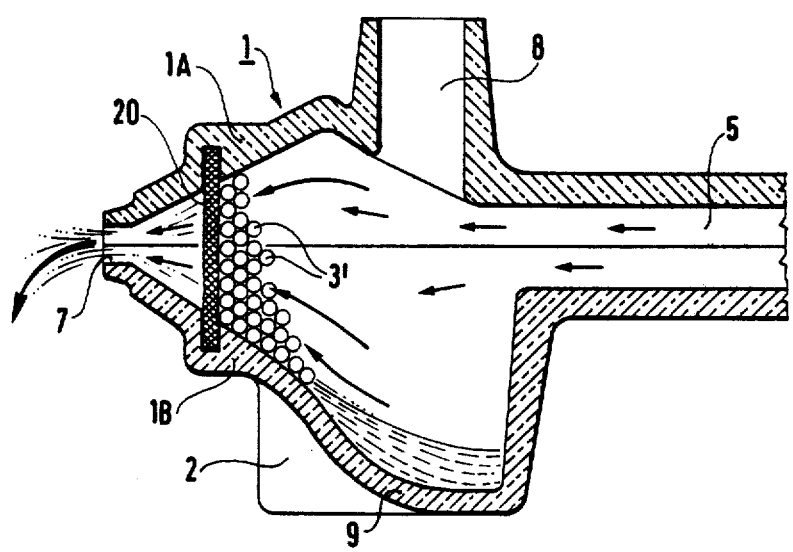

FIGS. 5A and 5B illustrate the case where each peripheral cell 2 of the rotor 1 includes not just a single bead but a plurality of small beads 3' whose diameter is practically of the order of 10 to 20 microns. Further, reference 20 designates a barrier which is suitable for retaining the beads during rotation of the apparatus, said barrier being built in or stuck in notches provided in the portions 1A and 1B which constitute the rotor 1. Advantageously, such a barrier is of the molecular filter type.

Consequently, each peripheral cell 2 provided with the beads 3' associated therewith is disposed under a supply means (the beads of each cell possibly corresponding to a particular dosage).

FIG. 5B corresponds to the moment when the rotor starts rotating and when the washing liquid is injected. It shows that centrifuging has the effect of driving out the excess reagent via the peripheral orifice 7 and of moving the beads 3' up the inclined bottom 9 until they are held by the barrier 20.

It should be noted that the numerous beads of small diameter appreciably increase reliability and the area over which reaction takes place.

Of course, the peripheral analysis cells may have a shape other than that illustrated in FIGS. 1 to 5B. In particular, they may have the shape illustrated in FIGS. 6 and 7 where the inner and outer surfaces are substantially parallel and where the outer surface has a side spout ending in the ejection orifice.

Figure 6:
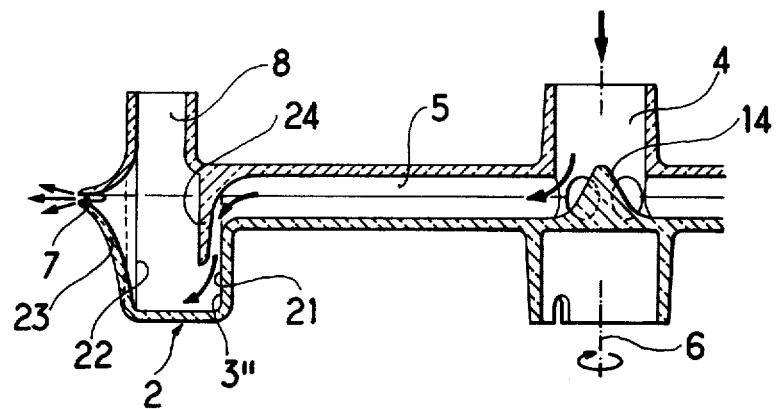
FIGS. 6 and 7 are a sectional and a perspective view, respectively, which illustrate the operation of the apparatus in the case where the support is formed by the wall of the lower portion of the cell.
Figure 7:
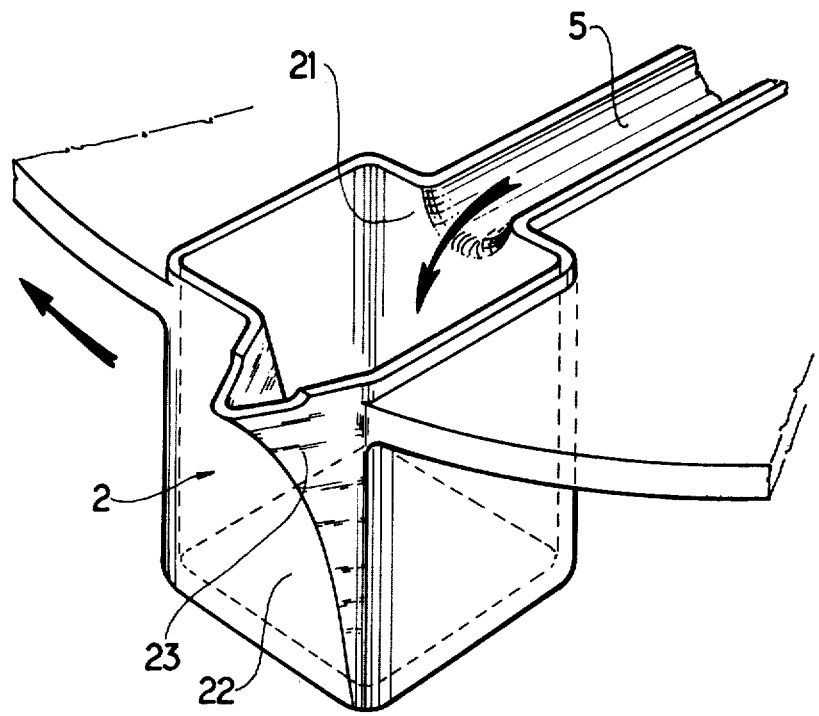

FIGS. 6 and 7 refer to the case where the reaction support surface is formed by the wall of the lower portion of the cell, but the general shape of the cell can be used when the reaction support surface is constituted by one or several beads.

The analysis apparatus has the same general configuration as previously.

The reaction support surface is here constituted by the wall of the lower portion 3'' of the cells 2 which is covered by a protein having anti-body type properties. The inner surface 21 and the outer surface 22 of the cell level with said lower portion are parallel. Further the outer surface 22 has a side spout 23 ending in the ejection orifice 7, said spout being positioned as illustrated at the rear of the cell relative to the direction of rotation.

The rotor is disposed under a supply means so as to inject in each cell 2 via its orifice 8 a (preferably calibrated) volume of a first reagent such as serum, plasma or any other biological liquid which contains the substance to be analysed; after said injection, the first reagent is allowed to stand during the required incubation period.

The rotor is then rotated and washing liquid is injected via the central orifice 4. Means 24 are provided at the outlets of the pipes 5 to form baffle plates so as to direct the washing liquid correctly towards the bottom of the cell. For each cell, the effect of centrifuging is to drive out the excess reagent via the peripheral orifice 7. Further, the washing liquid whose proper distribution is promoted by a central protrusion 14 passes via the radial pipes 5 and thoroughly washes the walls of the lower portion of each cell 2, said liquid escaping via the peripheral orifices 7, removal thereof being complete due to the side spout 23.

After washing, the lower portions of the cell may optionally be dried by stopping the washing liquid supply while maintaining centrifuging.

These operations are then repeated with the second reagent which contains a protein on which is fixed a biological indicator e.g. an enzyme or a radioisotope. Once the rotor is stopped, a simultaneous analysis can be carried out, either directly using a Geiger counter if radioisotope is used or indirectly if coloured reagent is used perhaps in conjunction with a reaction stopping agent.

The parallelism of the inner and outer surfaces of the lower portion of the cell obviously facilitates the photometric analysis of each cell.

However, it is quite evident that the peripheral cells can have other shapes, in particular shapes corresponding to those illustrated in FIGS. 1 to 5B.

The operation of the apparatus in accordance with the invention shows that great simplicity and high reliability are obtained since the treatments are very repeatable, and require little manipulation. By way of example, with the apparatus of the invention, the five simultaneous dosages required for a thyroid analysis can be performed rapidly and simply. Further the versatility of said apparatus is illustrated by one possibility (among others), namely that of dividing the rotor into two zones to use some cells as controls and then to provide identical supports to carry out the same test for several clients, or alternatively provide different supports and to carry out several tests for the same client.

Lastly, it must be mentioned that the compactness of the apparatus is a considerable advantage since its diameter can be of the order of 5 cm.

I claim:

1. Analysis apparatus comprising an analysis rotor, said rotor including firstly a plurality of peripheral cells each of which contains a solid reaction support, said solid reaction support holding successively, a quantity of first reagent such as a biological liquid which contains the substance to be analysed, and then a quantity of second reagent which contains a protein on which a biological indicator is fixed, and secondly means for conveying a washing liquid to each cell, and wherein each of said cells is provided with a peripheral orifice for removing liquid and having an upper portion provided with a reagent inlet orifice and a lower portion which accomodates said reagent.

2. Analysis apparatus according to claim 1, wherein the means which convey the washing liquid are constituted by a central inlet orifice and radial pipes leaving and connecting said central orifice to each of the peripheral cells.

3. Analysis apparatus according to claim 2, wherein the radial pipes are in a plane which is essentially perpendicular to the axis of rotation of the apparatus.

4. Analysis apparatus according to claim 2 or 3, wherein the radial pipes communicate with each cell substantially at the same level as the peripheral orifice through which liquid is removed from said cell.

5. Analysis apparatus according to claim 1, wherein the inlet orifices for the reagent are equidistant from the axis of the rotor.

6. Analysis apparatus according to claim 1, wherein the walls which define the lower portion of each cell allow simultaneous photometric analysis.

7. Analysis apparatus according to claim 1, wherein the rotor is formed by superposing two coaxial rotor portions whose contacting peripheral edges define directly the peripheral orifices of the cells.

8. Analysis apparatus according to claim 1, wherein the reaction support is formed by at least one bead.

9. Analysis apparatus according to claim 8, wherein the support is constituted by a plurality of beads of relatively small diameter, and a barrier is disposed in each cell adjacent said peripheral removal orifice, said barrier being suitable for retaining the beads during said centrifuging.

10. Analysis apparatus according to claim 9, wherein said barrier is of the molecular filter type.

11. Apparatus according to claim 9 or 10, wherein the diameter of said beads lies between substantially 10 and 20 microns.

12. Apparatus according to claim 1, wherein the reaction support is constituted by the wall of the lower portion of each cell.

13. Analysis apparatus according to claim 8, wherein the bottom of each cell is generally inclined so that firstly the lower portion of the cell has a volume which is sufficient to accommodate the reaction support and the quantity of reagent which covers it and secondly said support is guided substantially up to the level of the peripheral orifice of said cell during centrifuging.

14. Analysis apparatus according to claim 1, wherein the inner and outer surfaces of the cells are substantially parallel, the outer surface further having a side spout ending in the removal orifice and allowing the complete removal of the washing liquid during centrifuging.

15. Analysis apparatus according to claim 14, wherein the spout is located at the rear of the cell relative to the rotation direction.

* * * * *